United States Patent
Li et al.

(10) Patent No.: US 8,328,354 B2
(45) Date of Patent: Dec. 11, 2012

(54) SYSTEMS AND METHODS FOR BINOCULAR VISION DIAGNOSIS AND TREATMENT

(75) Inventors: Geng Li, Shatin (HK); Yeung-Ming Chow, Tai Po (HK); Man-Hong Balwin Chan, Ma Wan (HK); Tat-Hoi Lee, Sheung Shui (HK); Chung-Kong Cheung, Kowloon (HK)

(73) Assignee: Hong Kong Applied Science and Technology Research Institute Co., Ltd., Hong Kong (CN)

( * ) Notice: Subject to any disclaimer, the term of this patent is extended or adjusted under 35 U.S.C. 154(b) by 180 days.

(21) Appl. No.: 12/886,357

(22) Filed: Sep. 20, 2010

(65) Prior Publication Data

US 2012/0069296 A1 Mar. 22, 2012

(51) Int. Cl.
*A61B 3/08* (2006.01)
*A61B 3/00* (2006.01)

(52) U.S. Cl. .......... 351/201; 351/200
(58) Field of Classification Search ........... 351/200–246
See application file for complete search history.

(56) References Cited

U.S. PATENT DOCUMENTS

| | | | |
|---|---|---|---|
| 4,155,632 A | 5/1979 | Wolbarsht | |
| 5,026,151 A | 6/1991 | Waltuck et al. | |
| 5,452,030 A | 9/1995 | Feinbloom | |
| 5,671,087 A | 9/1997 | Kawamura | |
| 5,764,340 A * | 6/1998 | Hofeldt | 351/201 |
| 5,936,663 A * | 8/1999 | Tabata et al. | 348/51 |
| 7,290,878 B1 * | 11/2007 | Hofeldt | 351/201 |
| 2007/0200927 A1 | 8/2007 | Krenik | |
| 2008/0062338 A1 | 3/2008 | Herzog et al. | |
| 2009/0096983 A1 | 4/2009 | Provitola | |

* cited by examiner

*Primary Examiner* — Mohammed Hasan
(74) *Attorney, Agent, or Firm* — Fulbright & Jaworski L.L.P.

(57) ABSTRACT

A device for at least one of diagnosis and treatment of binocular vision disorders is disclosed. The device comprises a portable, wearable viewing apparatus that includes a left eye electronic display and a right eye electronic display, a dual data channel input, wherein each data channel corresponds to a respective one of the left eye and right eye electronic displays, a left eye adjustable optic structure adjusting a view of the left eye electronic display, and a right eye adjustable optic structure adjusting a view of the right eye electronic display. The device also includes a controller in communication with the dual data channel input that renders a first image at the left eye electronic display and a second image at the right eye electronic display simultaneously, in which the first and second images are different, and a memory in communication with the controller configured to store at least one of a diagnosis image pattern and a treatment image pattern for said binocular vision disorders for display by the viewing apparatus.

19 Claims, 8 Drawing Sheets

| RENDERING A FIRST IMAGE AT THE LEFT EYE ELECTRONIC DISPLAY AND A SECOND IMAGE AT THE RIGHT EYE ELECTRONIC DISPLAY SIMULTANEOUSLY FOR A HUMAN PATIENT | — 1001 |

REPEATING 1001 ACCORDING TO AT LEAST ONE OF:

1. A PROCEDURE FOR DIAGNOSING THE HUMAN PATIENT WITH AT LEAST ONE BINOCULAR VISION DISORDER

2. A REGIMEN FOR TRAINING THE HUMAN PATIENT TO PERFORM BINOCULAR COMBINATION WITH TWO EYES;

3. A REGIMEN FOR TRAINING THE HUMAN PATIENT TO PERFORM STEREO COMBINATION WITH TWO EYES;

SYSTEMS AND METHODS FOR BINOCULAR VISION DIAGNOSIS AND TREATMENT

TECHNICAL FIELD

The present description is related, generally, to diagnosis and treatment of binocular vision disorders and, more specifically, to a portable and wearable device for diagnosing and treating binocular vision disorder.

BACKGROUND OF THE INVENTION

Binocular vision disorder is an inability of a person to fuse the two images from his or her two eyes into one coherent image (binocular combination) and/or to get a Three-Dimensional (3-D) dimensional view with depth perception (stereo acuity). Binocular vision disorder is especially common among amblyopia and strabismus patients but it is not limited to amblyopia and strabismus patients.

Figure 1:
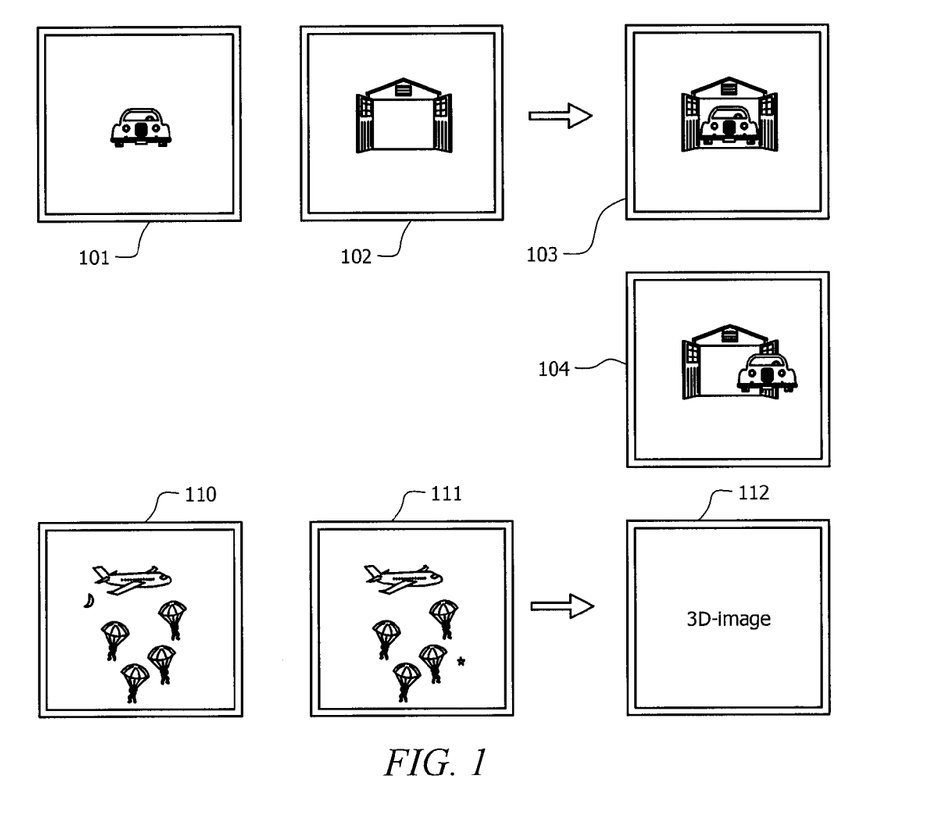
FIG. 1 is an illustration of normal binocular vision and binocular vision disorder.

FIG. 1 is an illustration of normal binocular vision and binocular vision disorder. When presented with slide 101 at the left eye and slide 102 at the right eye, a person with healthy binocular vision will see image 103, which is a combined 2-D image. By contrast, a person who has binocular vision disorder may see image 104, which is improperly combined (in this case, not aligned).

When presented with slides 110 and 111 (which look similar but are slightly different so as to give a stereo 3-D effect), a person with healthy binocular vision will correctly perceive the 3-D quality of combined image 112. On the other hand, a person with binocular vision disorder will not correctly perceive the combined image as 3-D.

Most studies focus on monocular deficits in the amblyopic eye. Most amblyopia treatment products are for treating amblyopia in spatial vision for improvement of visual acuity, spatial frequency and contrast sensitivity. For stroke patient recovery, treatment tends to focus on motor exercise. There is a general lack of treatment for binocular vision capability.

One conventional technique for treating binocular vision capability includes the synoptophore. When using a synoptophore, a patient rests his or her head in the device, aligned with two viewing apparatuses—one for each eye. A healthcare worker manually inserts slides into the viewing portions to show each eye a different image. Prisms may be used to change a viewing angle at an eye or to change an optical axis relative to a geometric axis. The patient attempts to combine the images into either a 2-D image or a 3-D image. The synoptophore can be used to diagnose binocular vision disorder by giving the healthcare worker an indication of the disability. For instance, people with normal vision will see the fused image without changing the viewing angle to a large extent, but eye patients may require the help of adjusting the viewing angle by the synoptophore in order to see the fused image. Additionally or alternatively, the healthcare worker can use the synoptophore to treat the disability. In one example, the healthcare worker applies a regimen to train the patient's eyes and mind to perform binocular capability and to see in true 3-D. The regimen may include showing a series of slides, and perhaps adjusting an angle of view or a geometrical axis of the slides, to gradually acclimate the patient to binocular combination and 3-D viewing.

Synoptophores are not an optimal device for treatment and diagnosis. Synoptophores are table-top instruments that are fairly large and heavy. Thus, synoptophores are not portable, and a patient must travel to a clinic for treatment, perhaps several times a week. Furthermore, synoptophores are expensive and almost completely manual.

BRIEF SUMMARY OF THE INVENTION

Various embodiments are directed to systems and methods using a portable, wearable device to treat and/or diagnose binocular vision disorder. In one example, a device includes a pair of goggles that has two displays (e.g., Liquid Crystal Displays (LCDs))—one for each eye. The two displays operate independently to show different images to each eye simultaneously. Additional features may include apparatuses to change a viewing angle of at least one of the displays and/or to change an optical axis of at least one of the displays.

Continuing with the example, the displays are controlled by one or more microprocessors that implement a diagnostic procedure or a treatment regimen. For instance, the device may display a series of differing images on each of the displays so as to provide images that can be combined in 2-D or 3-D and are relevant to binocular combination and/or stereo acuity. Such images can be used to diagnose or treat binocular vision disorder. Also, the device may modify viewing angles and/or axes in accordance with a diagnosis procedure or a treatment regimen. Images to be displayed and instructions for displaying images and analyzing treatment may be stored in computer-readable memory and accessed by the one or more microprocessors.

Various embodiments may include one or more advantages over conventional techniques. For instance, various embodiments provide a device that can be used at home or other convenient locations for a user, thereby minimizing the need for frequent travel. Also, smaller, lighter, and more automated devices may in some instances be manufactured more inexpensively than the heavy, manual synoptophores currently in use. Embodiments may be used to treat and/or diagnose amblyopia, strabismus, and other visual disorders affecting binocular vision.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 2:
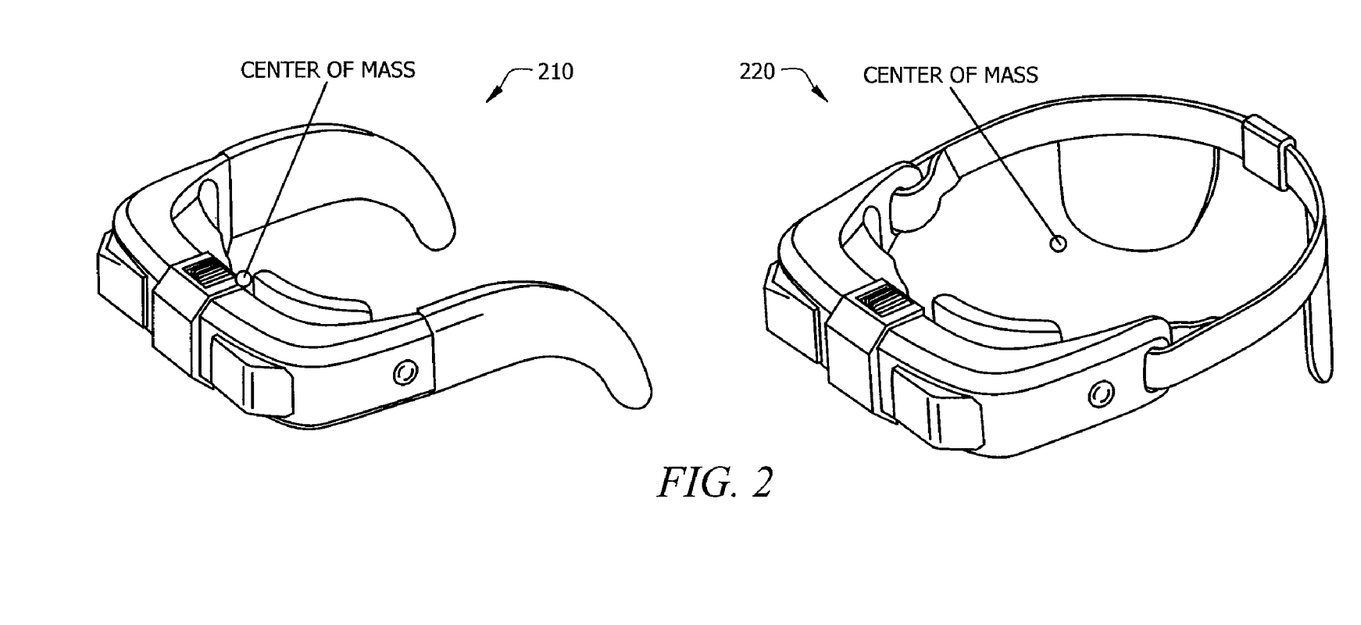
FIG. 2 is an illustration of exemplary embodiments of a device adapted according to aspects of the invention.

FIG. 2 is an illustration of exemplary embodiments of a device adapted according to aspects of the invention. FIG. 2 shows goggles 210, according to a first embodiment, and goggles 220, according to a second embodiment. Goggles 210 are smaller and lighter, whereas goggles 220 are a little larger and heavier but designed to fit better and to have a center of mass near the middle of the patient's head. The scope of embodiments is not limited to those shown in FIG. 2, as other embodiments may take other forms.

The example embodiments of FIG. 2 illustrate a novel binocular vision system in a compact display platform, e.g., a portable electronic LCD goggle, and an inventive implementation of adjustable optics to achieve binocular fusion for diagnosis and treatment of binocular vision disorder in amblyopia and strabismus patients and other persons with visual disorders due to brain defects. Various implementations and methods of use are described further below.

Figure 3:
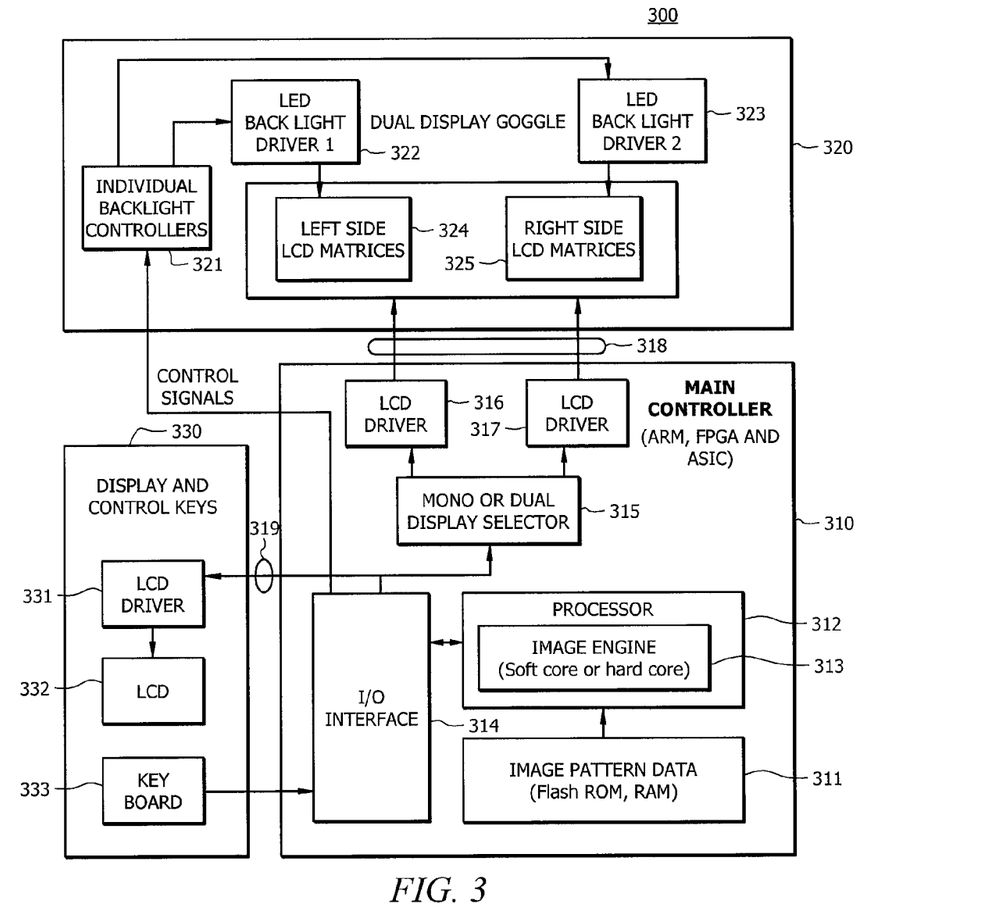
FIG. 3 is an illustration of an exemplary diagnosis/treatment system adapted according to one embodiment of the invention.

FIG. 3 is an illustration of an exemplary diagnosis/treatment system 300 adapted according to one embodiment of the invention. System 300 includes main controller 310, goggles 320, and user interface device 330. Main controller 310 may be integral to goggles 320 or separate from goggles 320, depending on the configuration. Main controller 310 controls goggles 320 and user interface device 330, as explained further below.

Main controller 310 can be implemented using any of a variety of processor-based devices. Examples include, but are not limited to, a general-purpose processor, a Field Programmable Gate Array, an application specific integrated circuit (ASIC), a Digital Signal Processor (DSP), and the like. Main controller 310 includes computer readable medium 311 (e.g., a hard drive media, optical media, RAM, EPROM, EEPROM, tape media, cartridge media, flash memory, ROM, memory stick, and/or the like) that stores image pattern data. Processor 312 accesses computer readable medium 311 retrieve, and possibly store, image pattern data for use in treatment and/or diagnosis of binocular vision disorder. After image data has been processed by image engine 313, it is passed to input/output (I/O) interface 314, which acts as an interface to LCD drivers 316, 317, and 331. I/O interface 314 also sends control signals to backlight controllers 321 and receives control signals from user interface device 330.

Display selector 315 allows for selection of stereo or mono vision. When stereo is selected, two different images are sent to the two LCD drivers 316, 317. When mono is selected, the same image is sent to LCD drivers 316, 317. Display selection 315 may be accessed e.g., by a button, on goggles 320 and/or by user interface device 320.

LCD drivers 316, 317 provide dual data channel input 318 to goggles 320, where dual data channel input 318 carries a respective video signal to each respective LCD matrix 324, 325. Goggles 320 includes back light controllers 321 and respective backlight drivers 322, 323 which are in communication with individual LCD matrices 324, 325. In other words, each eye of the patient sees a display that can be individually controlled to show a same or different image as one shown to the other eye. Additionally, each display can be turned off to rest both eyes or to show a single image to a single eye (e.g., in occlusion therapy). Individual brightness control for each of the displays may also be used in binocular vision training, where a blinking light is used to draw a patient's attention to one of the image pictures for binocular fusion training.

User interface device 330 is a device that may be separate from, or integral to, goggles 320 and may be separate from, or integral to, main controller 310. User interface device 330 receives data output 319 from main controller 310, where data output 319 transfers video data representative of the images shown to the patient. Such images are processed by LCD driver 331 to be rendered upon LCD matrix 332. User interface device 330 also has input device 333, which can be a keyboard, touchpad, joystick, or other kind of device for receiving input from a user.

User interface device 330 provides a way for a healthcare worker, or other person, to view the images that are seen by the patient and to control operation of goggles 320 in some instances. For example, a healthcare worker may view the images as they are seen by the patient and communicate with the patient at the same time, perhaps adjusting the series of images in response to the communication with the patient. The person can adjust the sequence of images, by using input device 333, which provides control data to main controller 310.

While system 300 is shown using an LCD display system, the scope of embodiments is not so limited. Any suitable display technology now known or later developed may be adapted for use in some embodiments. For instance, Organic Light Emitting Diode (OLED) displays are becoming more popular for video systems and can be used in some embodiments in addition to, or instead of, LCD displays.

Figure 4:
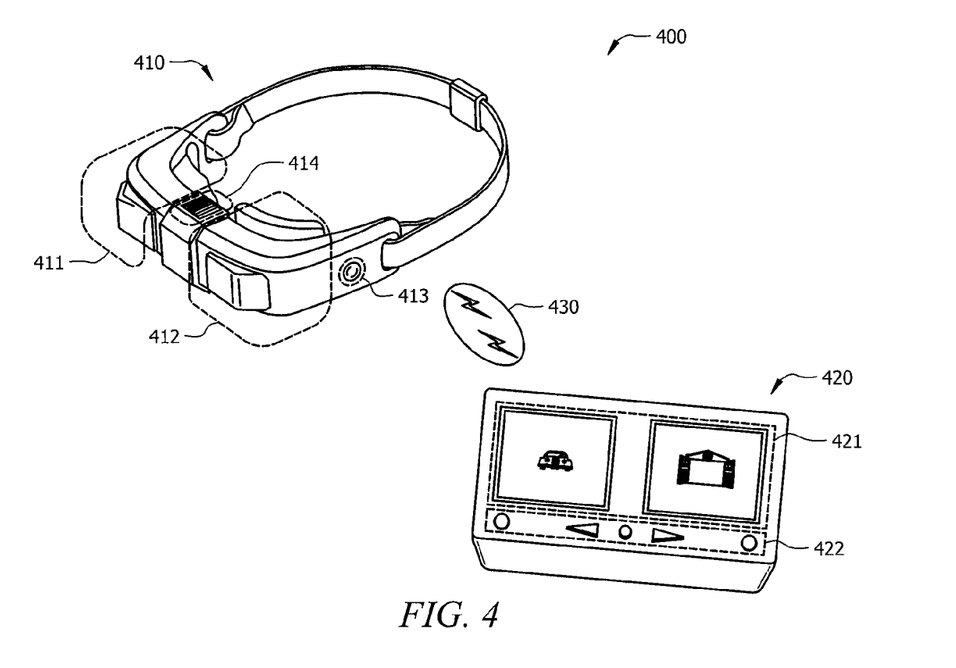
FIG. 4 is an illustration of an exemplary diagnosis/treatment system adapted according to one embodiment of the invention.

FIG. 4 is an illustration of an exemplary diagnosis/treatment system 400 adapted according to one embodiment of the invention. The embodiment shown in FIG. 3 can be implemented according to the concept illustrated in FIG. 4, or in other ways, if desired.

Diagnosis/treatment system 400 includes goggles 410 and user interface device 420. In this example, the main controller is integral to goggles 410 and is not shown for convenience. Goggles 410 include two independent displays 411, 412 so that each eye can be treated independently. Goggles 410 also have on/off button 413 and fit adjustment wheel 414.

User interface device 420 has display 421, which shows the images seen by the patient and may also show control information (e.g., control menus with selectable options) in some instances. User interface device 420 also has keypad 422 to receive user input.

User interface device 420 and goggles 410 may communicate over any suitable link now known or later developed. For instance, in some embodiments, a wired link may be used. In this example, user interface device 420 and goggles 410 are shown communicating with a wireless link 430, which may be a Bluetooth™ link, an 802.11 link, an infrared link, or other suitable link.

Diagnosis and therapy for binocular vision disorder not only includes showing different images to each eye or changing a light intensity. Such techniques may also include changing an angle of view of at least one of the displays and/or changing an optical axis of at least one of the displays. Various embodiments provide mechanisms for changing angles and axes for each eye.

Figure 5A:
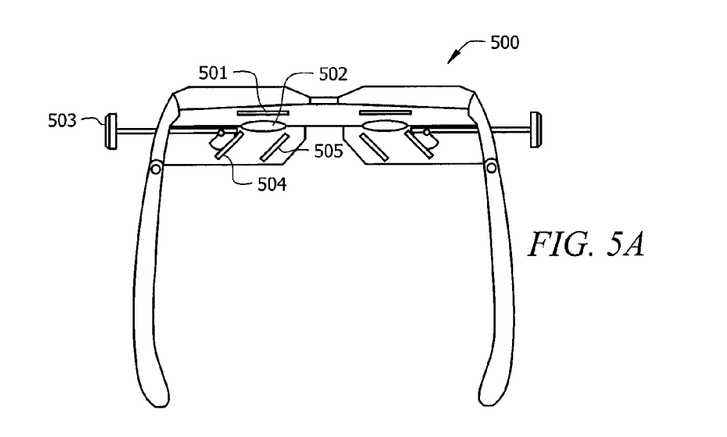
FIGS. 5A and B are an illustration of an exemplary vision system, adapted according to one embodiment of the invention.
Figure 5B:
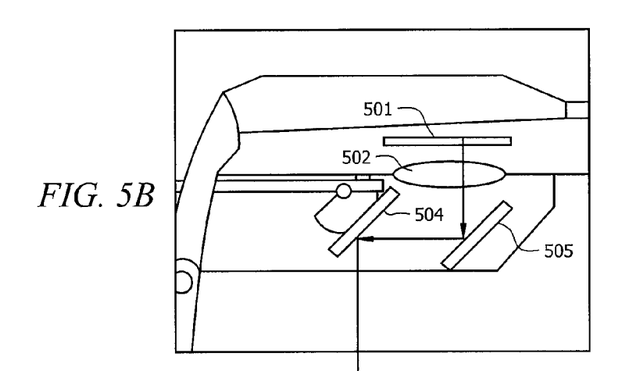

FIGS. 5A and B are an illustration of exemplary vision system 500, adapted according to one embodiment of the invention. Specifically, FIG. 5A shows vision system 500 from a distance, whereas FIG. 5B shows a close-up view of an adjustable mirror system utilized by system 500 to change an angle of viewing for a left-eye display. It is understood that the adjustable mirror system for the right-eye operates in a manner similar to that described below for the adjustable mirror system for the left eye.

As shown in FIG. 5A, the left-eye mechanism includes lens 502, which focuses light from display 501. The light from lens 502 strikes fixed mirror 505 and reflects from fixed mirror 505 to adjustable mirror 504. Adjustable mirror 504 directs the light at a desired angle to the patients' left eye. The position of adjustable mirror 504, and hence the angle of the light as it enters the patient's eye, is changed using mechanism 503. Mechanism 503 is shown in this example as a manual mechanism, and it is understood that such mechanism may be implemented as an electromechanical mechanism in other embodiments that provide for automation of adjustment of mirror 504.

Figure 6:
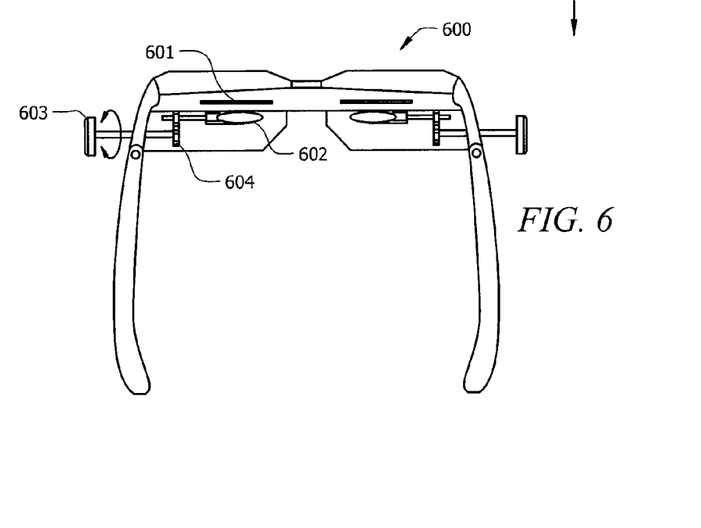
FIG. 6 is an illustration of an exemplary vision system, adapted according to one embodiment of the invention for providing lens de-centering.

FIG. 6 is an illustration of an exemplary vision system 600, adapted according to one embodiment of the invention for providing lens de-centering. System 600 includes a mechanism to adjust a geometric axis with respect to an optical axis to thereby shift a virtual image seen by a patient. System 600 includes display 601 and lens 602 positioned in front of display 601. Lens 602 is moved horizontally by use of the adjusting mechanisms that has a gear chain assembly 604 and an adjustment handle 603. The gear chain assembly is shown in this example as a manual mechanism, and it is understood the gear chain assembly may be implemented as an electromechanical mechanism in other embodiments that provide for automation of adjustment of lens 602. It is understood that the lens de-centering mechanism for the right eye may work in a same or similar manner to that described above for the left eye.

Figure 7:
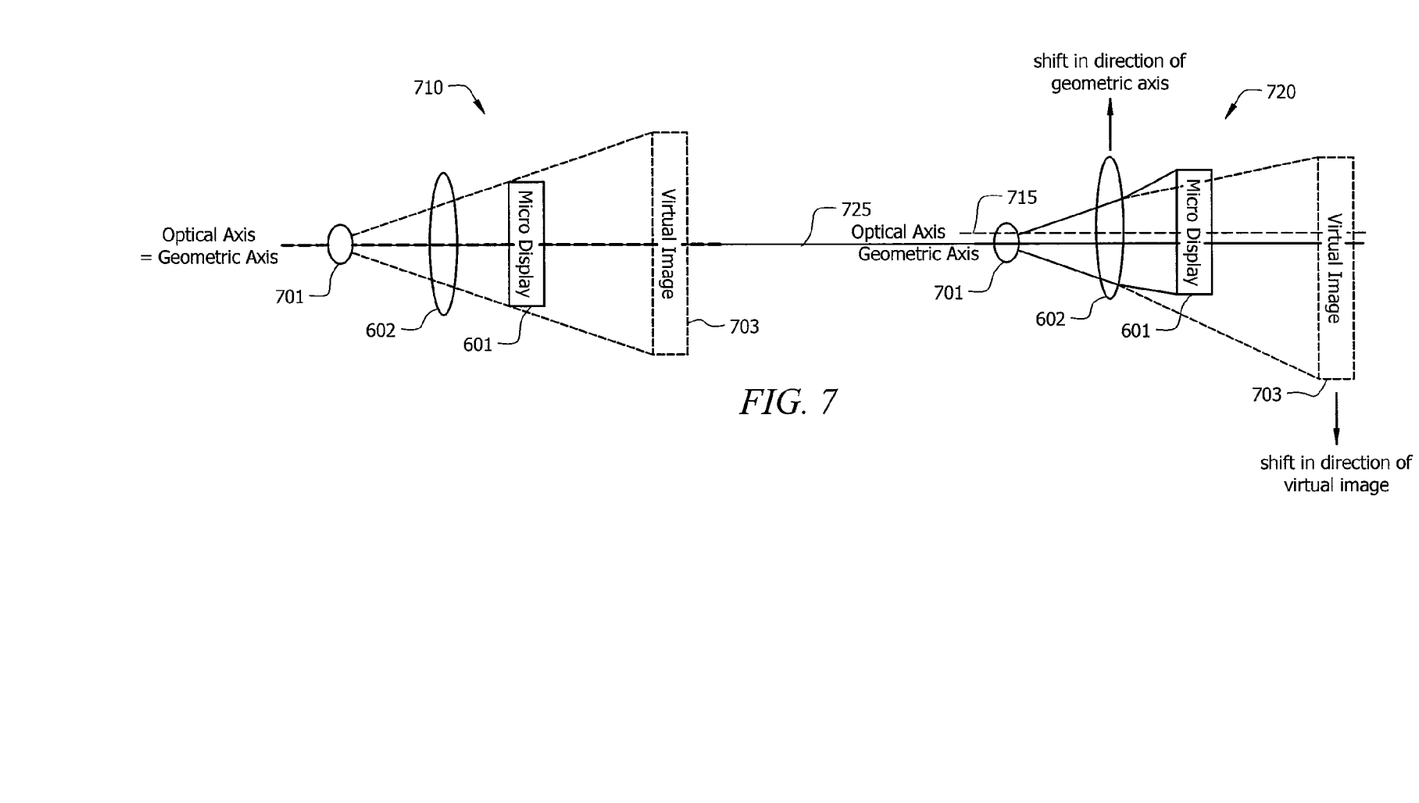
FIG. 7 is an example illustration of lens de-centering according to one embodiment of the invention.

FIG. 7 is an example illustration of lens de-centering according to one embodiment of the invention. Scenario 710 shows alignment of geometric axis 725 with optical axis 715 of eye 701. In scenario 710, virtual image 703 and display 601 are also aligned with optical axis 715. Persons who have healthy binocular vision see the virtual image aligned as shown in scenario 710 with no lens de-centering. Some patients with binocular vision disorder may not have the same alignment.

In scenario 720, optical axis 715 is shifted relative to geometric axis 725. As shown in FIG. 7, the relative shift also shifts virtual image 703 as seen by the patient. Some diagnostic and treatment procedures include having the patient adjust the viewing distance and viewing angles until alignment is achieved, to teach the patient's eyes a different alignment geometry, etc.

Adjusting viewing angles and adjusting positions of the virtual image are tools that can be used in diagnosis and treatment of binocular vision disorders. In fact, the mechanisms of FIGS. 5 and 6 are for the same purpose, i.e. they are different mechanisms for achieving variable viewing angles. Furthermore, although not shown herein, lens 502 and lens 602 may also include a zoom lens feature for adjusting virtual display image distance.

Figure 11:
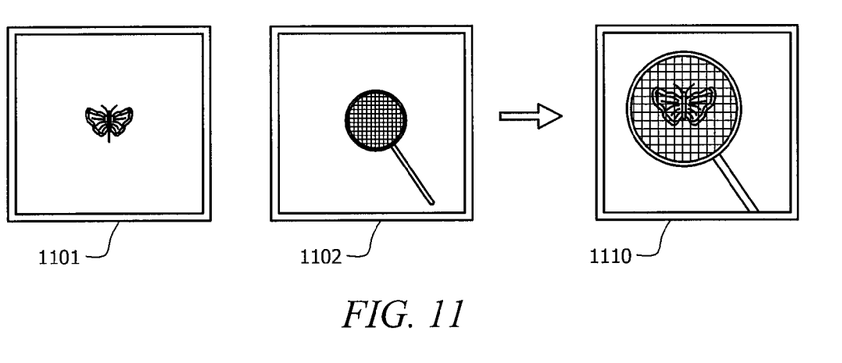
FIG. 11 is an illustration of example images for use in a binocular fusion test according to one embodiment of the invention.

Various embodiments of the invention provide for methods to use a device, such as the devices described above. In one example diagnosis regimen, there are three levels. The first level is for coarse/qualitative binocular fusion test, using, e.g., slides 101, 102 of FIG. 1. The second level is for a fine/quantitative binocular fusion test with grid dimension in the slides, such as that shown in FIG. 11, where left eye image 1101 and right eye image 1102 are combined by a person with normal vision to see combined image 1110. The third level is for stereo-acuity, using e.g., slides 110, 111 of FIG. 1.

In an example treatment regimen, there are three levels. In the first level, the patient undergoes monocular training, such as occlusion therapy, to strengthen the weaker eye. The first level may be especially applicable to amblyopia patients, though other patients may skip the first level and go to the second level.

Figure 8:
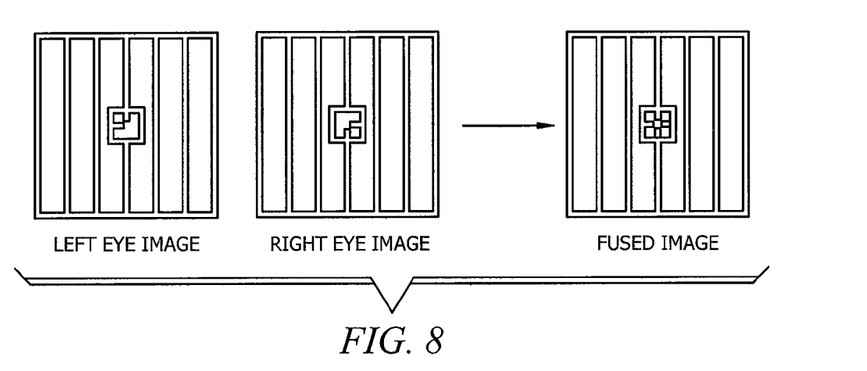
FIG. 8 shows an example of a left eye image and a right eye image usable in level two training.

In the second level, the patient undergoes binocular combination/fusion training. In level two, the patient trains to build the capability to position the two eyes at the right place so that the patient can see the image field un-separated. An example of a left eye image and a right eye image usable in level two training is shown in FIG. 8. FIG. 8 also shows a properly fused image. Training may include turning on and off two individual backlights (one for each eye) at different frequencies and time durations. The image provided to the weak eye stays on at a longer duration, whereas the image provided to the dominant eye stays on at a shorter duration. The exercise reminds the patient that the "+" should be formed in the middle of the box.

Figure 9:
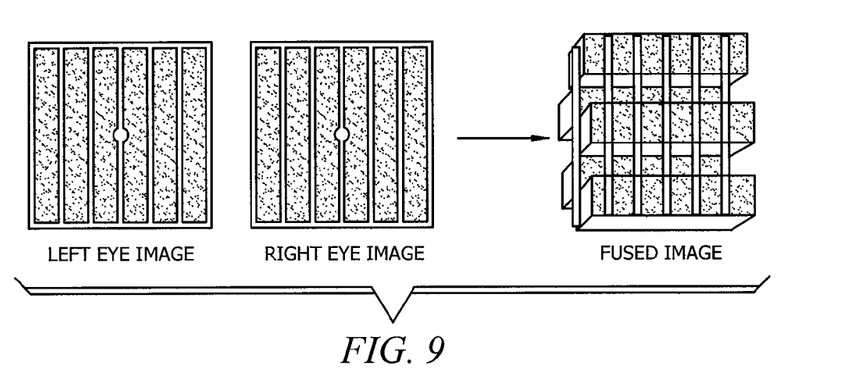
FIG. 9 shows an example of a left eye image and a right eye image usable in level three training.

In level three, the patient undergoes stereo acuity training. An example of a left eye image and a right eye image usable in level three training is shown in FIG. 9. FIG. 9 also shows a properly fused image. Level three training presents two different images to each eye in a way that the patient's brain must combine the two images in order to successfully identify the whole picture. Training may include showing a series of different images to the patient so as to exercise and incrementally improve the patient's stereo acuity. In one example, the viewing angles and image distances are kept changing back and forth for stimulating/reminding the visual cortex to process the image signal at the weak eye side.

Figure 10:
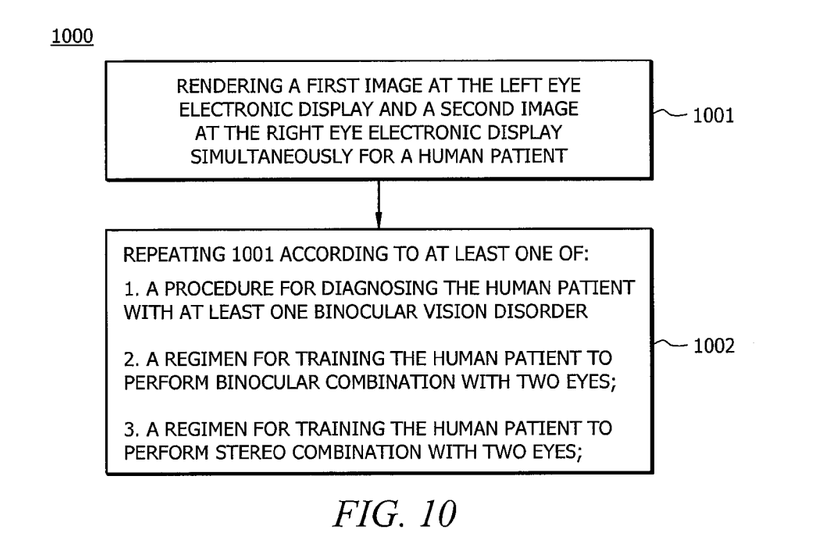
FIG. 10 is an illustration of an exemplary process, adapted according to one embodiment of the invention.

FIG. 10 is an illustration of exemplary process 1000, adapted according to one embodiment of the invention. Process 1000 may be performed by a patient, a healthcare worker, a clinic, or other person using any of the devices described above.

In block 1001, a first image is rendered at the left eye electronic display, and a second image is rendered at the right eye electronic display simultaneously for a human patient. In other words, the patient sees two different images at the same time. Examples include those shown in FIGS. 1, 8, and 9.

In block 1002, the actions of block 1001 are repeated according to at least one of: a procedure for diagnosing the human patient with at least one binocular vision disorder; a regimen for training the human patient to perform binocular combination with two eyes; and a regimen for training the human patient to perform stereo combination with two eyes; and. Examples of binocular combination training and stereo acuity training are described in more detail above.

Block 1002 may include adjusting a viewing angle and/or an optical axis of at least one of the images. The scope of embodiments is not limited to the exact process shown in FIG. 10. Other embodiments may add, delete, rearrange, or modify actions according to a training or diagnosis procedure. For instance, in one example, a user may employ the device for diagnosis and treatment in the same sitting or may employ the device for stereo acuity training and binocular combination training in the same sitting.

Various embodiments include advantages over previous devices. For instance, the example devices described above are more robust than the other devices shown in Table 1, below. In Table 1, below, the first entry describes an example embodiment of the present invention, whereas the other entries describe other devices. The other devices have fixed viewing optics and are adapted for entertainment use rather than vision diagnosis and treatment.

TABLE 1

| Company/ Country | Model Name | Image Input | Adjustable Eyes- Separation | Viewing Optics | Image Size | Programmable Chip |
|---|---|---|---|---|---|---|
| ASTRI Hong Kong | v-Trainer | Dual | Y | Variable distance and angle | Variable | Y |
| Prober China | EVG920D | Mono | N | Fixed 2 m | Fixed 80 inches | N |
| Prober China | IMV260 | Mono | N | Fixed 1.2 m | Fixed 50 inches | N |
| Vuzix US | VR920 | Mono | N | Fixed 2.7 m | Fixed 62 inches | N |
| I-O Display US | i-glasses i3pc | Mono | N | Fixed 3 m | Fixed 70 inches | N |

Furthermore, various embodiments have advantages over the conventional synoptophore. For instance, the synoptophore is not readily movable, thereby requiring that patients travel to a clinic to receive treatment. On the other hand, various embodiments of the present invention are portable and can be worn by a patient. In some scenarios, a patient may be sent home with a device (such as that shown in FIG. 2) to receive a training regimen at home. Some embodiments may also be cheaper to manufacture than a synoptophore.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A device for at least one of diagnosis and treatment of binocular vision disorders, the device comprising:
   a portable, wearable viewing apparatus that includes:
      a left eye electronic display and a right eye electronic display;
      a dual data channel input, wherein each data channel corresponds to a respective one of the left eye and right eye electronic displays;
      a left eye adjustable optic structure adjusting a view of the left eye electronic display;
      a right eye adjustable optic structure adjusting a view of the right eye electronic display; and
   a controller in communication with the dual data channel input that renders a first image at the left eye electronic display and a second image at the right eye electronic display simultaneously, in which the first and second images are different;
   a memory in communication with the controller configured to store at least one of a diagnosis image pattern and a treatment image pattern for said binocular vision disorders for display by the viewing apparatus; and
   a mechanism coupled to at least one of the left eye adjustable optic and the right eye adjustable optic, the mechanism configured to adjust a viewing angle of at least one of the first and second images using at least one of the left eye and right eye adjustable optics structures.

2. The device of claim 1 in which the adjustable optic structures adjust a viewing distance of the first and second images.

3. The device of claim 1 in which the binocular vision disorders include at least one of amblyopia and strabismus.

4. The device of claim 1 further comprising:
   a data output configured to connect to a separate user interface module, the data output transferring data corresponding to images shown by the left eye and right eye electronic displays.

5. The device of claim 1 in which the left eye electronic display comprises a first Liquid Crystal Display (LCD) module, and in which the right eye electronic display comprises a second LCD module.

6. The device of claim 5 further comprising:
   a first backlight unit in communication with the first LCD module; and
   a second backlight unit in communication with the second LCD module.

7. The device of claim 5 further comprising:
   a first LCD driver unit in communication with the first LCD module; and a second LCD driver unit in communication with the second LCD module.

8. The device of claim 5 configured with a weight distribution such that a center of gravity of the device is substantially in a center of a patient's head.

9. A method of using a device, wherein the device includes a wearable viewing apparatus that has a left eye electronic display and a right eye electronic display, a left eye adjustable optic structure adjusting a view of the left eye electronic display, and a right eye adjustable optic structure adjusting a view of the right eye electronic display, the method comprising:
  (a) rendering a first image at the left eye electronic display and a second image at the right eye electronic display simultaneously for a human patient;
  (b) repeating (a) according to a regimen for training the human patient to perform binocular combination with two eyes, and adjusting a viewing angle of at least one of the first and second images using at least one of the left eye and right eye adjustable optics structures.

10. The method of claim 9 in which the first and second images form a third image when combined.

11. The method of claim 10 in which the third image comprises a two-dimensional fused image.

12. The method of claim 9 in which (b) includes:
turning on and off each of a right eye backlight and a left eye backlight at different frequencies and time durations, wherein the first or second image provided to a weaker one of the eyes stays on at a longer duration than does the first or second image provided to a stronger one of the eyes.

13. A method of using a device, wherein the device includes a wearable viewing apparatus that has a left eye electronic display and a right eye electronic display, a left eye adjustable optic structure adjusting a view of the left eye electronic display, and a right eye adjustable optic structure adjusting a view of the right eye electronic display, the method comprising:
  (a) rendering a first image at the left eye electronic display and a second image at the right eye electronic display simultaneously for a human patient;
  (b) repeating (a) according to a regimen for training the human patient to perform stereo combination with two eyes, and adjusting a viewing angle of at least one of the first and second images using at least one of the left eye and right eye adjustable optics structures.

14. The method of claim 13 in which the first and second images form a third image when combined.

15. The method of claim 14 in which the third image comprises a three-dimensional fused image that cannot be recognized until combined.

16. The method of claim 13 in which (b) includes:
adjusting viewing angles and image distances of the first and second images to stimulate a visual cortex of the human patient to process an image signal at a weak eye side.

17. A method of using a device, wherein the device includes a wearable viewing apparatus that has a left eye electronic display and a right eye electronic display, a left eye adjustable optic structure adjusting a view of the left eye electronic display, and a right eye adjustable optic structure adjusting a view of the right eye electronic display, the method comprising:
  (a) rendering a first image at the left eye electronic display and a second image at the right eye electronic display simultaneously for a human patient;
  (b) repeating (a) according to a procedure for diagnosing the human patient with at least one binocular vision disorder, and adjusting a viewing angle of at least one of the first and second images using at least one of the left eye and right eye adjustable optics structures.

18. The method of claim 17 in which the first and second images form a third image when combined.

19. The method of claim 17 in which the procedure for diagnosing the human patient includes:
performing a coarse/qualitative binocular fusion test;
performing a fine/quantitative binocular fusion test; and
performing a stereo-acuity test.

* * * * *